US007694552B2

(12) United States Patent
Khuri-Yakub et al.

(10) Patent No.: US 7,694,552 B2
(45) Date of Patent: Apr. 13, 2010

(54) HIGH QUALITY FACTOR RESONATORS FOR LIQUID IMMERSION BIOLOGICAL AND CHEMICAL SENSORS

(75) Inventors: Butrus T. Khuri-Yakub, Palo Alto, CA (US); Goksen G. Yaralioglu, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 291 days.

(21) Appl. No.: 12/069,730

(22) Filed: Feb. 11, 2008

(65) Prior Publication Data

US 2008/0190181 A1 Aug. 14, 2008

Related U.S. Application Data

(60) Provisional application No. 60/901,200, filed on Feb. 12, 2007.

(51) Int. Cl.
*G01N 29/00* (2006.01)
*G01N 15/06* (2006.01)

(52) U.S. Cl. ..................... 73/64.53; 73/61.75; 73/61.79

(58) Field of Classification Search ................ 73/64.53, 73/579, 61.75, 61.79
See application file for complete search history.

(56) References Cited

U.S. PATENT DOCUMENTS 5,705,399 A 1/1998 Larue
5,936,150 A 8/1999 Kobrin et al.
6,247,354 B1 6/2001 Vig et al.
6,260,408 B1 7/2001 Vig et al.
6,906,450 B2 6/2005 Tamayo De Miguel et al.
2004/0150428 A1 * 8/2004 Itoh et al. ...................... 327/1

* cited by examiner

*Primary Examiner*—Hezron Williams
*Assistant Examiner*—Nathaniel Kolb
(74) *Attorney, Agent, or Firm*—Lumen Patent Firm

(57) ABSTRACT

A mechanical resonator capable of providing an intrinsically high mechanical quality factor in immersion is provided. The resonator includes a membrane attached at its perimeter to a frame, such that a front side of the membrane is in contact with the liquid, and the back side of the membrane is not in contact with the liquid or the frame. The membrane can act as a mechanical resonator. The quality factor of this resonator is enhanced by providing a pressure release boundary region on the frame in proximity to the membrane and in contact with the liquid. The pressure release boundary region provides a soft boundary condition, in the sense that a mechanical impedance on the solid side of the solid-liquid interface is less than the liquid mechanical impedance. Providing such a soft boundary condition reduces the mechanical energy loss due to excitation of waves in the liquid, thereby improving resonator quality factor. Such high-Q resonators are particularly useful for sensor applications.

17 Claims, 6 Drawing Sheets

102
104
106
108

HIGH QUALITY FACTOR RESONATORS FOR LIQUID IMMERSION BIOLOGICAL AND CHEMICAL SENSORS

CROSS REFERENCE TO RELATED APPLICATIONS

This application claims the benefit of U.S. provisional patent application 60/901,200, filed on Feb. 12, 2007, entitled "High Quality Factor Resonators for Liquid Immersion Biological and Chemical Sensors", and hereby incorporated by reference in its entirety.

FIELD OF THE INVENTION

This invention relates to sensors suitable for liquid immersion applications.

BACKGROUND

Resonant mechanical structures are commonly employed as sensor elements for detecting the presence of biological or chemical analytes. Such detection is typically based on functionalizing the resonant mechanical structure such that the analyte or analytes of interest can bind to the mechanical resonator, if they are present. The binding of analytes to the mechanical resonator alters the resonant frequency of the mechanical resonator due to the mass of the bound analytes. Measurement of the resonant frequency of the mechanical resonator can thereby provide a sensitive indication as to the presence of the analytes.

In order for such sensors to provide high sensitivity, it is important for the mechanical resonator to have low mechanical loss, which is frequently expressed in terms of the resonator having a high quality factor (i.e., high Q). High Q results in a reduction of measurement noise, thereby improving sensitivity. However, it is challenging to provide high-Q mechanical resonators for use in liquid immersion applications, because liquid loading of the mechanical resonator due to immersion tends to significantly and undesirably decrease resonator Q.

In U.S. Pat. No. 6,906,450, resonator Q in immersion is electronically enhanced by providing electronic feedback control of the mechanical resonator. However, imposing a requirement on the sensor control electronics to provide appropriate Q-enhancing feedback may conflict with other sensor design considerations. Accordingly, it would be an advance in the art to provide mechanically resonant sensors having intrinsically high Q in fluid immersion.

SUMMARY

A mechanical resonator capable of providing an intrinsically high mechanical quality factor in immersion is provided. The resonator includes a membrane attached at its perimeter to a frame, such that a front side of the membrane is in contact with the liquid, and the back side of the membrane is not in contact with the liquid or the frame. The membrane can act as a mechanical resonator. The quality factor of this resonator is enhanced by providing a pressure release boundary region on the frame in proximity to the membrane and in contact with the liquid. The pressure release boundary region provides a soft boundary condition, in the sense that a mechanical impedance on the solid side of the solid-liquid interface is less than the liquid mechanical impedance. Providing such a soft boundary condition reduces the mechanical energy loss due to excitation of waves in the liquid, thereby improving resonator quality factor. Such high-Q resonators are particularly useful for sensor applications.

DETAILED DESCRIPTION

Figure 1A:
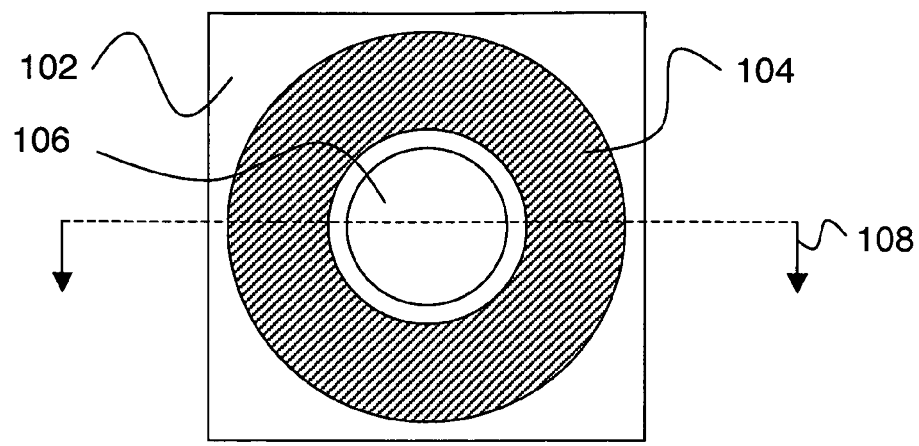
FIG. 1*a* shows a top view of an embodiment of the invention.
Figure 1B:
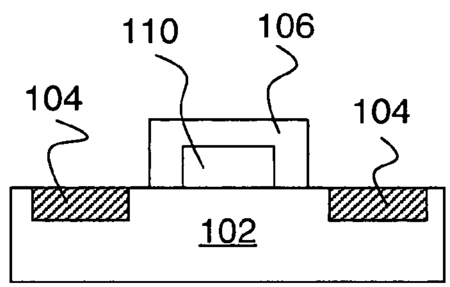
FIGS. 1*b-c* show side views of two embodiments of the invention.
Figure 1C:
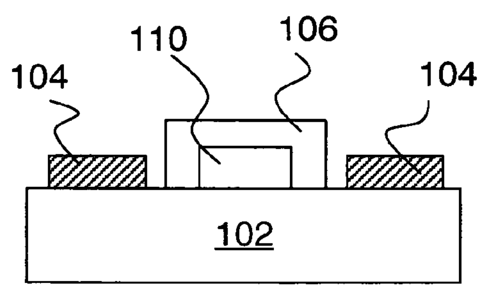

FIGS. 1*a-b* show top and side views respectively of an embodiment of the invention. This embodiment is a sensor subassembly including a membrane 106, a frame 102 attached to the perimeter of membrane 106, and a pressure release boundary region 104 disposed on frame 102 in proximity to membrane 106. The pressure release boundary region is a key aspect of the invention that is described in detail below. However, it is convenient to first consider FIG. 1*d*, which shows a sensor including the sensor subassembly of FIGS. 1*a-b*, prior to describing the significance of the pressure release boundary region. FIGS. 1*b-c* shows side views along line 108 of FIG. 1*a*.

Figure 1D:
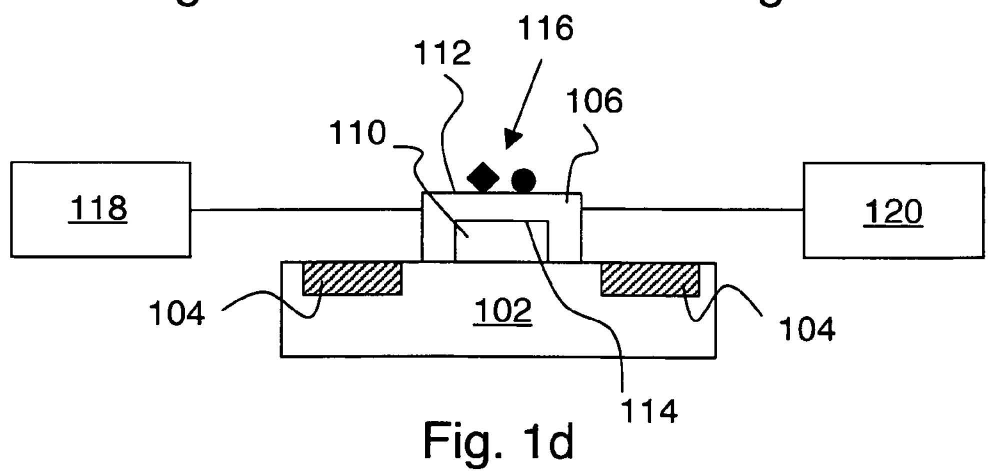
FIG. 1*d* shows a sensor according to an embodiment of the invention.

During operation of the sensor of FIG. 1*d*, a sensor surface 112 of membrane 106 is in contact with a fluid (typically a liquid), and a back surface 114 of membrane 106 is not in contact with the fluid. In other words, a liquid-free space 110 is formed behind membrane 106. Membrane 106 is driven to oscillate by energizing circuit 118, and a resonant frequency of membrane 106 is measured by sensing circuit 120. The presence of analytes 116 bound to sensor surface 112 of membrane 106 can be detected by measuring the shift in resonant frequency due to the mass of the bound analytes, typically by means of a displacement measurement.

As will become apparent below, practice of the invention does not depend critically on details of the membrane geometry, or on the means employed to measure membrane resonant frequency. Circular membranes are shown in the examples herein, but membranes according to embodiments of the invention can have any shape. Typical membranes have a diameter from tens of microns to hundreds of microns and a thickness on the order of microns. Decreasing membrane size tends to improve detection sensitivity, while increasing membrane size tends to increase Q, so detailed sensor design can consider a trade off of these two tendencies.

Displacement of membrane 106 can be measured by any technique, including but not limited to: optically, capacitively, magnetically, and piezoelectrically. For example, an optical interferometer can measure membrane displacement. Capacitance of a capacitor having an electrode on the membrane as one of its plates can be measured to provide a membrane displacement sensor. Motion of a metal coil on the membrane can be magnetically sensed to provide membrane displacement. Motion of a piezoelectric film affixed to the membrane can be electrically sensed to provide membrane displacement information. Atomic tip displacement sensing can also be employed. For example, variation in a tunneling current across a gap between membrane 106 and a reference electrode can be measured according to principles of tunneling microscopy. The atomic tip for such an approach can be disposed on membrane 106 or on the reference electrode. The reference electrode can be in the form of a cantilever.

Pressure release boundary region 104 is in contact with the fluid during sensor operation, and provides what is convenient to refer to as a "soft boundary condition" at the interface between the pressure release boundary region and the fluid. More precisely, such a soft boundary condition is defined as providing a mechanical impedance at the solid side of the solid-fluid interface that is less than the mechanical impedance of the fluid at this interface. Details of the shape or arrangement of the pressure release boundary region are not critical in practicing the invention. For example, pressure release boundary region 104 can be fully embedded in frame 102 as shown on FIG. 1*b*, or it can be disposed on top of frame 102 as shown on FIG. 1*c*, or any intermediate degree of embedding in frame 102 can be employed. More generally, any structure or device which provides a soft boundary condition as defined above can be regarded as a pressure release boundary region for practicing embodiments of the invention. Several exemplary implementations of pressure release boundary regions are described below.

Figure 2:
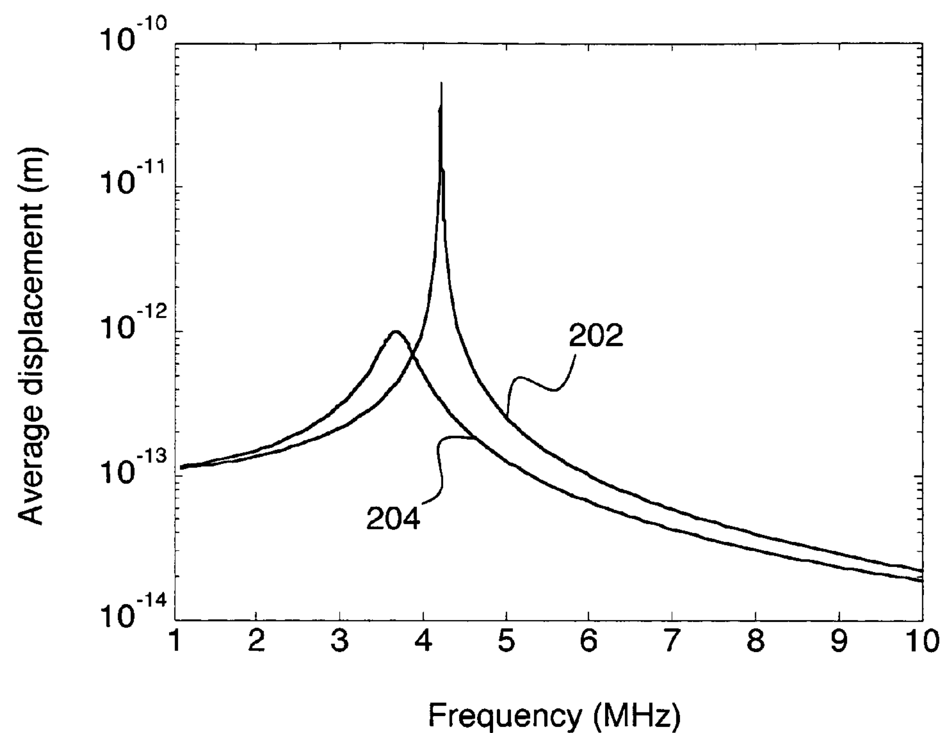
FIG. 2 shows average displacement vs. frequency for an immersed mechanical resonator surrounded by regions providing two different boundary conditions.

The importance of the boundary conditions provided near an immersed mechanical oscillator can be appreciated by considering the idealized displacement vs. frequency modeling results shown on FIG. 2. In this example, a harmonic pressure load is applied to a circular membrane fully supported at its perimeter and facing a liquid half space. Curve 204 (Q=9.3) is the result when the boundary condition around the membrane is idealized to be perfectly "hard" (i.e., no displacement of the solid). Curve 202 (Q=496.0) is the corresponding result when the boundary condition around the membrane is idealized to be perfectly "soft" (i.e., no pressure at the boundary, solid displacement follows displacement of the liquid).

As is evident from curves 202 and 204, perfectly soft boundary conditions make the resonator have much higher Q (i.e., sharper and higher peak) than perfectly hard boundary conditions. The physical reason for this dependence on boundary conditions near (but not on) the resonator itself is that such boundary conditions affect the efficiency with which acoustic waves are generated in the liquid by the oscillating membrane. Since such acoustic waves take energy away from the resonator, they provide a loss mechanism that decreases resonator Q. Such radiative energy loss is hindered by providing soft boundary conditions near the oscillating membrane.

Special measures are required to provide the desirable soft boundary conditions identified above, because typical materials for sensor construction (e.g., silicon, tungsten, aluminum) tend to have substantially higher mechanical impedances than typical liquids of interest, such as water. There are various approaches for providing soft boundary conditions in practice.

Figure 3A:
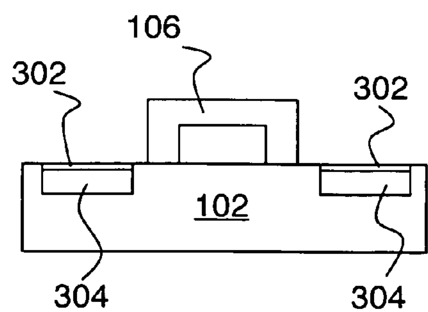
FIGS. 3*a-b* show two ways of providing soft boundary conditions.

One approach is shown in the side view of FIG. 3*a*. In this example, pressure release boundary region 104 of FIG. 1*b* is implemented by providing a thin annular secondary membrane 302 around membrane 106 and separating the fluid from a fluid free region 304. Membrane 302 preferably has a sufficiently low stiffness that the mechanical impedance provided by this structure at the solid side of the fluid-solid interface is substantially less than the fluid mechanical impedance at this interface. Since the back surface of secondary membrane 302 is not in contact with either the fluid or with frame 102, this arrangement can provide sufficiently low mechanical impedance.

Figure 3B:
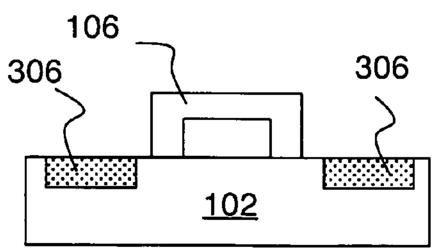

Another approach for providing pressure release boundary region 104 of FIG. 1*b* is shown in the side view of FIG. 3*b*. In this example, the pressure release boundary region is implemented by providing soft solid 306 as shown. Suitable compositions for solid 306 include, but are not limited to: silicone rubber (e.g., polydimethylsiloxane (PDMS)), room temperature vulcanizing (RTV) silicone rubber, RTV or PDMS like materials, polymers including air bubbles, silica aerogels, glass bubbles in an epoxy or RTV binder, and sealed balsa wood. Solid 306 can be provided as one or more layers. In cases where multiple layers are employed, the layers can be arranged to provide a passive mechanical resonator in analogy with the following membrane resonator examples.

Figure 4A:
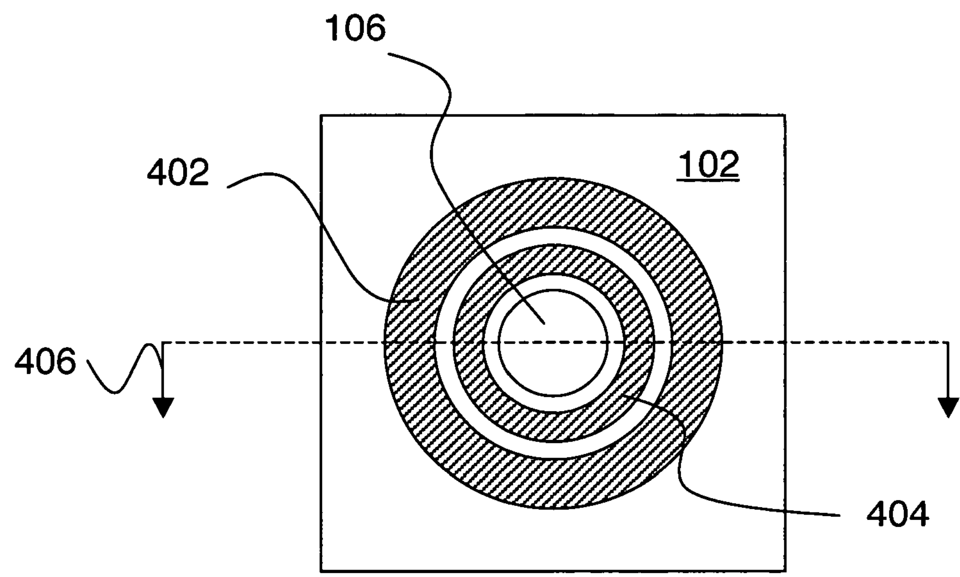
FIGS. 4*a-b* show an embodiment of the invention having soft boundary conditions provided by passive mechanical resonators.
Figure 4B:
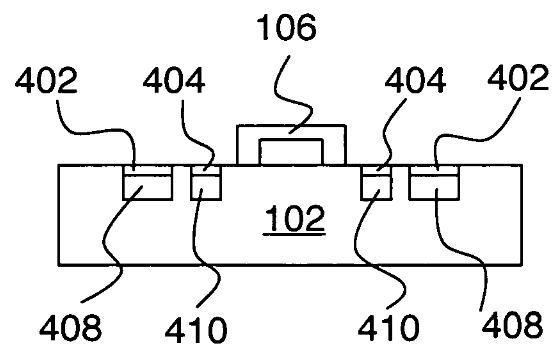

Another approach for providing soft boundary conditions is shown in the example of FIGS. 4*a-b*, where FIG. 4*b* is a side view along line 406 of FIG. 4*a*. In this example, the pressure release boundary regions are implemented as passive membrane resonators. Membrane 402 is disposed over fluid-free space 408, and membrane 404 is disposed over fluid-free space 410. A mechanical resonator provides a low (ideally zero) mechanical impedance at its resonant frequency. Therefore, by designing the passive resonators to have substantially the same resonant frequency as the active sensor membrane 106, suitable soft boundary conditions can be provided. In this context, it is helpful to define passive resonators as any resonators present in a sensor structure for which a displacement measurement is not performed to provide sensing, and active resonators as any resonators for which a displacement measurement is performed to provide sensing.

Mechanical impedances can be frequency-dependent. The above-stated requirement that the pressure release boundary region provide a lower mechanical impedance than the fluid is understood to apply to frequencies at or near the resonant frequency of the active resonator (e.g., the resonator formed by sensor membrane 106 in the preceding examples). It is not necessary to provide soft boundary conditions at frequencies well away from the resonant frequency of the active resonator, although some approaches (e.g., the examples of FIGS. 3*a-b*) tend to provide such broad-band softness.

Although changes of the resonant frequency of the active resonator occur during sensor operation, such changes tend to be very small fractional frequency changes. Therefore, any particular sensor will have a well-defined nominal resonant frequency of the active resonator which the passive resonators can be matched to.

Figure 5:
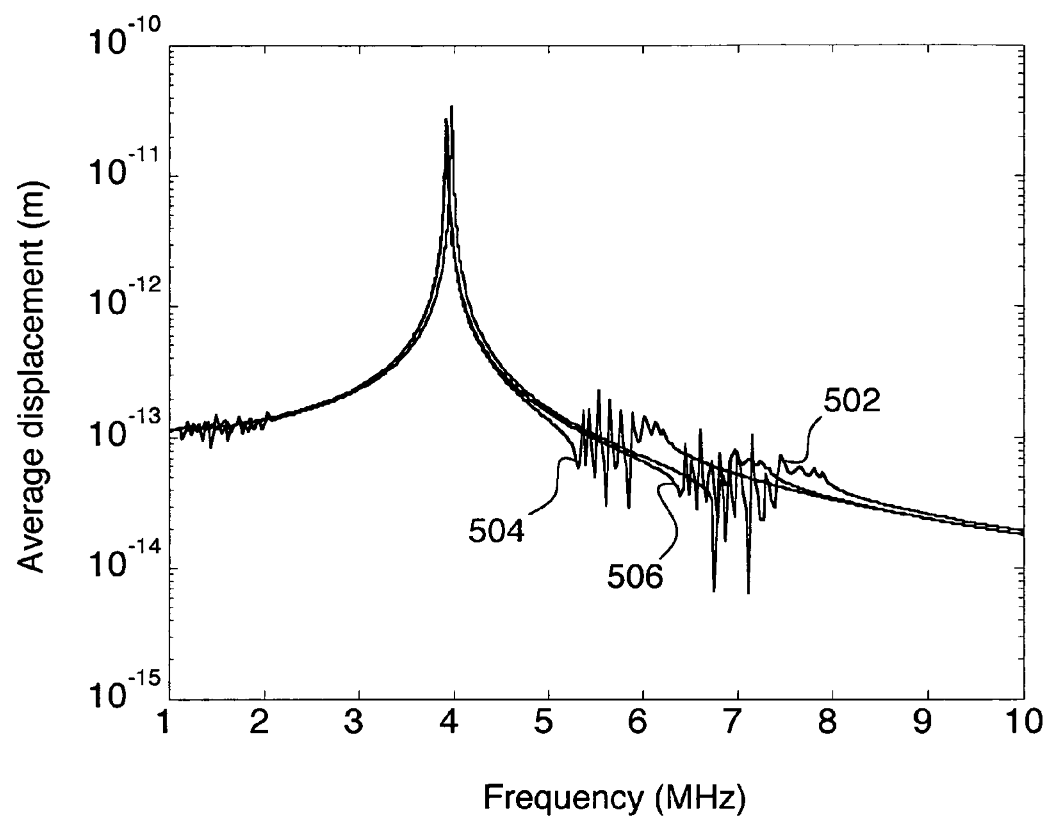
FIG. 5 shows average displacement vs. frequency for an immersed mechanical resonator surrounded by various arrangements of passive mechanical resonators.

FIG. 5 shows modeling results for three different passive resonator configurations of the kind shown on FIGS. 4*a-b*. In all cases, the active membrane has a 1 micron thickness and a 20 micron radius. For case 1, the passive resonators are concentric 40 micron wide, 1 micron thick annuli separated by idealized 0 micron wide solid pillars. For case 2, the passive resonators are concentric 44 micron wide, 1 micron thick annuli separated by idealized 0 micron wide solid pillars. For case 3, the passive resonators are concentric 41 micron wide, 1 micron thick annuli separated by 3 micron wide solid pillars. For all three cases, the number of concentric passive resonators was increased to a point where the boundary conditions assumed beyond the outermost passive resonator has no significant effect on the calculated results. Curves 502, 504 and 506 on FIG. 5 correspond to cases 1, 2, and 3 above, respectively. In all three cases, high Q (~350) in liquid immersion is obtained.

Figure 6:
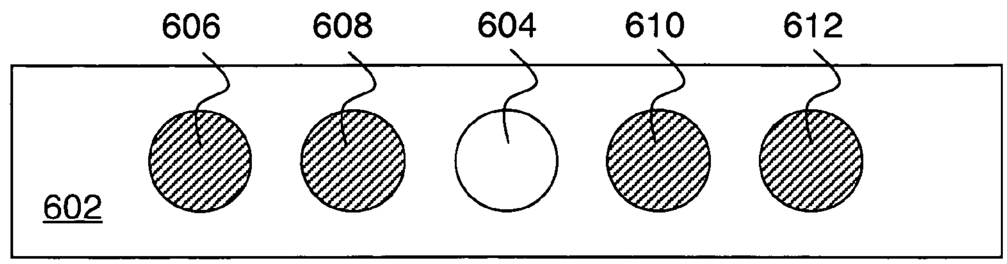
FIG. 6 shows a 1-D array of soft boundary condition regions centered on a sensor membrane.

Passive resonators can also be disposed in a 1-D or 2-D array centered on the active resonator. For example, FIG. 6 shows membrane 604 (i.e., the active resonator) centered in a 1-D array formed by passive resonators 606, 608, 610, and 612 on frame 602. In cases where multiple passive resonators are employed to provide soft boundary conditions, the passive resonators can be mechanically independent of each other, or they can be mechanically coupled such that they act as a system of coupled mechanical oscillators.

Figure 7A:
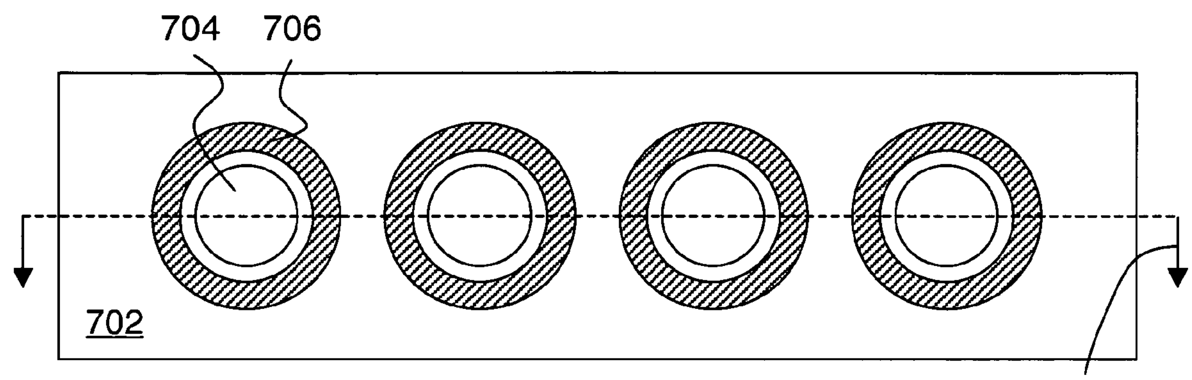
FIG. 7*a* shows a top view of a 1-D array of sensor membranes, each sensor membrane surrounded by a corresponding soft boundary condition region.
Figure 7B:
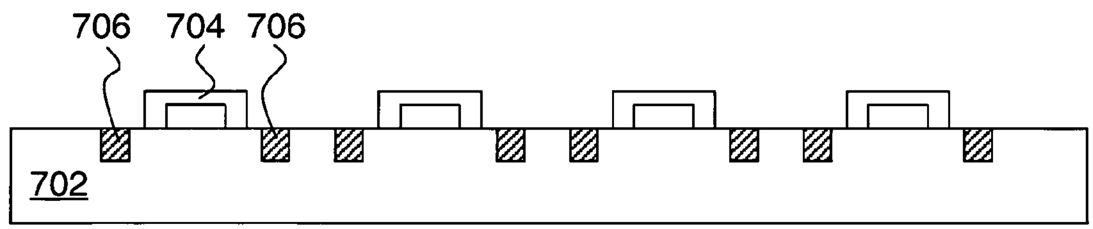
FIG. 7*b* shows a side view of the example of FIG. 7*a*.

In some embodiments of the invention, a 1-D or 2-D array of sensor elements is provided. FIG. 7*a* shows a top view of a 1-D array of sensor membranes on frame 702, each sensor membrane surrounded by a corresponding soft boundary condition region. FIG. 7*b* shows a side view of the example of FIG. 7*a*. One of the sensor membranes is referenced as 704, and its corresponding pressure release boundary region is referenced as 706. In cases where multiple sensor membranes are employed, the sensor membranes can be mechanically isolated from each other, or they can be mechanically coupled to act as a system of coupled mechanical resonators. In either case, increasing sensor Q by providing soft boundary conditions in accordance with principles of the invention can be helpful for improving sensor sensitivity. Practice of the invention is not critically dependent on geometrical details of the pressure release boundary regions. The example of FIG. 7*a* shows a pressure release boundary region around each active sensor membrane. It is also possible for the pressure release boundary region to surround the entire set of active sensor membranes (e.g., a single pressure release boundary region around the array of 4 sensors of the example of FIG. 7*a*).

Figure 7C:
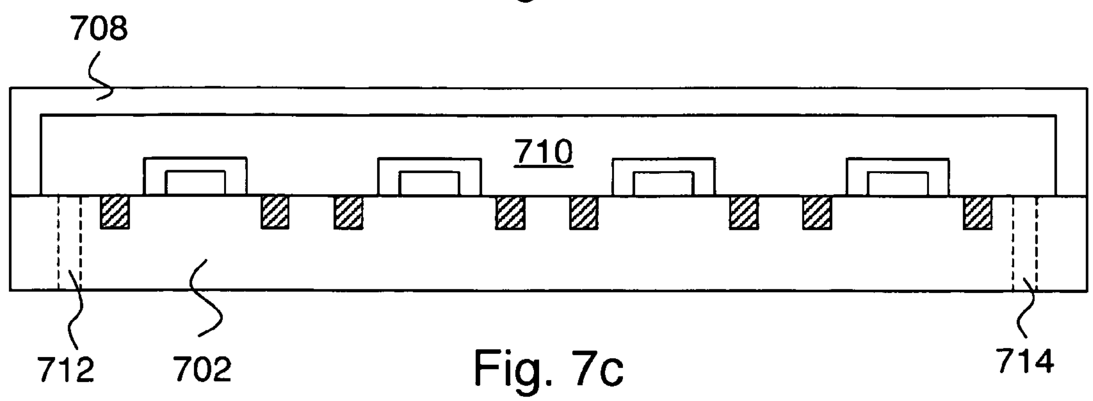
FIG. 7*c* shows a microfluidic device including the example of FIGS. 7*a-b*.

FIG. 7*c* shows a microfluidic device including the example of FIGS. 7*a*-*b*. In this example, a cap 708 is attached to frame 702 to form a microfluidic channel 710 through which a liquid containing analytes of interest can flow. Ports 712 and 714 enable the flow of liquid through this sensor.

Figure 8A:
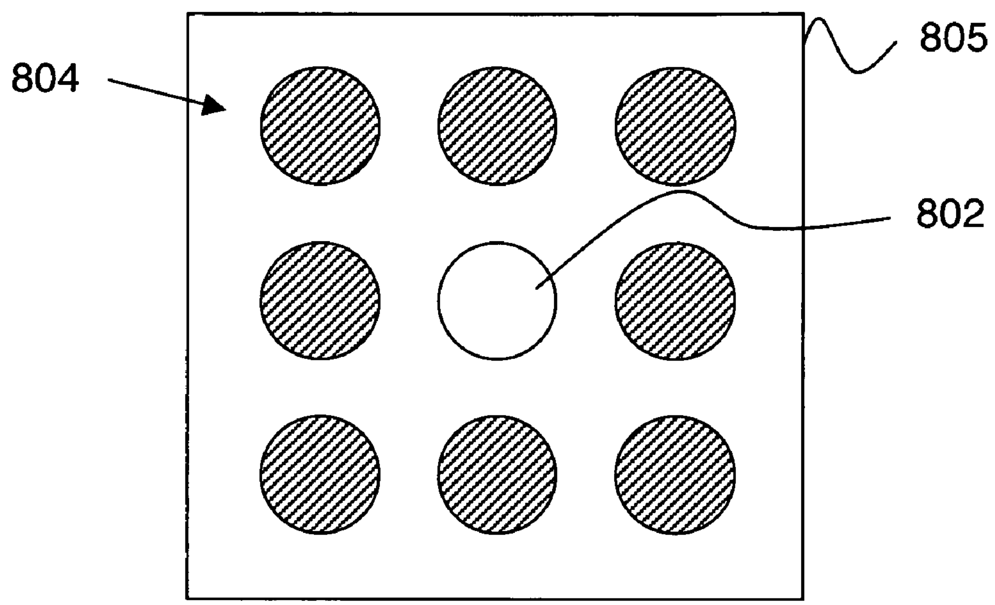
FIG. 8*a* shows a 2-D array of soft boundary condition regions centered on a sensor membrane.
Figure 8B:
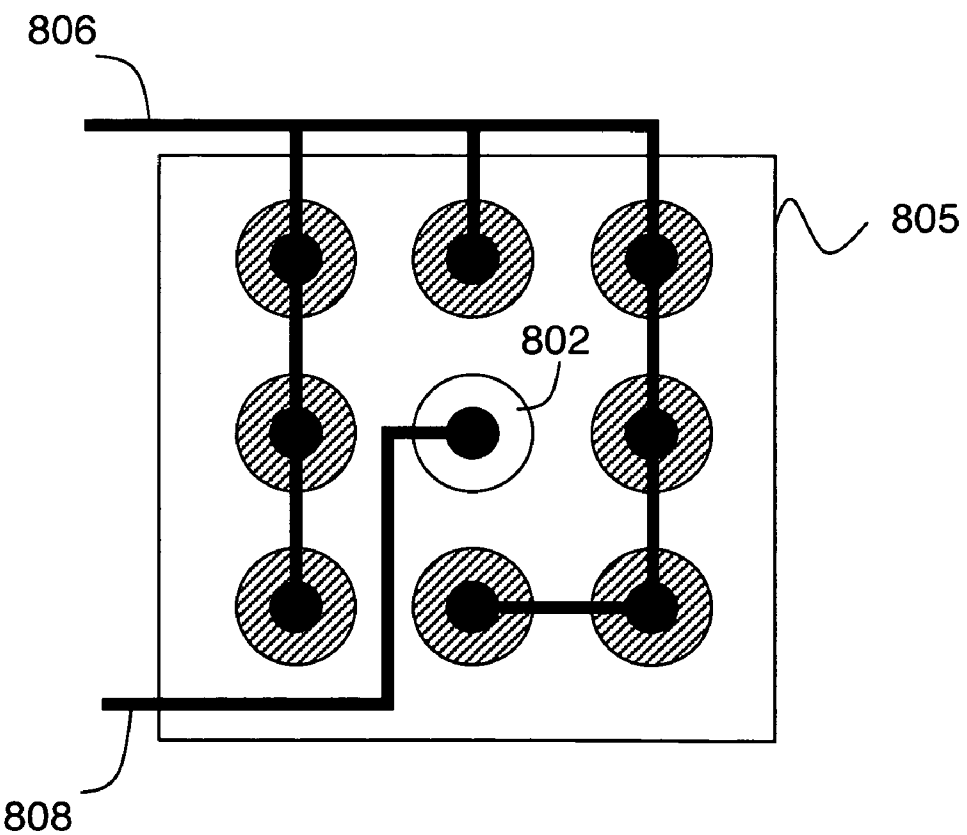
FIG. 8*b* shows electrodes in contact with array elements of the example of FIG. 8*a*.

FIG. 8*a* shows a 2-D array of soft boundary condition regions centered on a sensor membrane. Here active membrane 802 is surrounded by passive resonators 804 arranged as a 2-D array on frame 805. FIG. 8*b* shows electrodes in contact with array elements of the example of FIG. 8*a*. Electrode 808 is in contact with active resonator 802, and electrode 806 is in contact with passive resonators 804. Such electrodes can be helpful for matching the resonant frequency of passive resonators 804 to the resonant frequency of active resonator 802. For example, a DC bias is typically applied to active resonator 802 to make its oscillation more nearly sinusoidal. Such a DC bias shifts the resonant frequency of active resonator 802. In cases where active resonator 802 and passive resonators 804 have substantially the same mechanical construction, the same DC bias can be applied to passive resonators 804 in order to match the active and passive resonant frequencies. More generally, providing a DC bias to the passive resonators provides a helpful capability for adjusting and optimizing the soft boundary conditions provided by the passive resonators. In some cases, it may be preferred to have individual control of the DC bias at each passive resonator (by providing individual traces to each passive resonator), as opposed to common electrode 806 of the example of FIG. 8*b*.

The invention claimed is:

1. A sensor subassembly for use in fluid immersion applications, the sensor subassembly comprising:

one or more membranes, each said membrane having a sensor surface and a back surface facing away from said sensor surface, wherein each said sensor surface is in contact with a fluid during operation of said sensor subassembly, and wherein each said back surface is not in contact with said fluid during operation of said sensor subassembly;

a frame around said one or more membranes and attached to perimeters of said one or more membranes, whereby each of said one or more membranes can act as a mechanical resonator during operation of said sensor subassembly;

one or more pressure-release boundary regions, disposed on said frame in proximity to said one or more membranes and in contact with said fluid during operation of said sensor subassembly;

wherein said pressure-release boundary regions have a smaller mechanical impedance than said fluid at interfaces between said pressure-release boundary regions and said fluid.

2. The sensor subassembly of claim 1, wherein said one or more pressure-release boundary regions each comprise one or more layers of solid material disposed on said frame.

3. The sensor subassembly of claim 1, wherein said one or more pressure-release boundary regions comprise an annular secondary membrane surrounding said one or more membranes, wherein said secondary membrane has a front surface in contact with said fluid during operation of said sensor subassembly and a back surface facing away from said front surface, wherein said back surface is not in contact with said fluid or with said frame during operation of said sensor subassembly.

4. The sensor subassembly of claim 1, wherein said one or more pressure-release boundary regions comprise one or more passive mechanical resonators, each of said passive mechanical resonators having substantially the same mechanical resonant frequency as said membrane.

5. The sensor subassembly of claim 4, wherein said one or more passive resonators are in the form of distinct annular rings centered on said one or more membranes.

6. The sensor subassembly of claim 4, wherein said passive resonators are arranged as a two-dimensional array centered substantially on said one or more membranes.

7. The sensor subassembly of claim 4, wherein said passive resonators are arranged as a one-dimensional array centered substantially on said one or more membranes.

8. The sensor subassembly of claim 4, wherein one or more of said passive resonators has a mechanical resonant frequency that can be tuned by application of a DC voltage.

9. The sensor subassembly of claim 4, wherein said passive mechanical resonators are mechanically coupled to act as coupled mechanical resonators.

10. The sensor subassembly of claim 1, wherein said fluid comprises a liquid.

11. The sensor subassembly of claim 1, wherein said one or more membranes are mechanically coupled to act as coupled mechanical resonators.

12. The sensor subassembly of claim 1, wherein said pressure-release boundary regions have a smaller mechanical impedance than said fluid at a resonant frequency of said one or more membranes.

13. A sensor comprising:

a sensor subassembly according to claim 1;

an energizing circuit providing power to drive mechanical oscillation of said one or more membranes; and a sensing circuit providing a measurement of a resonant frequency of said one or more membranes.

14. The sensor of claim 13, wherein said sensor surfaces are treated to be capable of binding one or more analyte species that may be present in said fluid.

15. The sensor of claim 14, wherein said measurement of said resonant frequency of said one or more membranes is responsive to the presence of bound analytes on said sensor surfaces by way of a shift of said resonant frequency due to the mass of analytes bound to said sensor surfaces.

16. The sensor of claim 13, wherein said sensing circuit provides said measurement of a resonant frequency of said membrane by measuring a displacement of said one or more membranes.

17. The sensor of claim 16, wherein said displacement of said one or more membranes is measured according to a technique selected from the group consisting of: atomic tip displacement sensing, optical displacement sensing, piezo-electric displacement sensing, and magnetic displacement sensing.

* * * * *